United States Patent [19]

Hasselbrack

[11] Patent Number: 4,620,548
[45] Date of Patent: Nov. 4, 1986

[54] PAP SMEAR T-ZONE SAMPLER

[75] Inventor: Robert Hasselbrack, Seattle, Wash.

[73] Assignee: Accupap, Inc., Seattle, Wash.

[21] Appl. No.: 693,830

[22] Filed: Jan. 23, 1985

Related U.S. Application Data

[63] Continuation of Ser. No. 405,783, Aug. 6, 1982, abandoned, which is a continuation-in-part of Ser. No. 152,375, May 22, 1980, abandoned, which is a continuation-in-part of Ser. No. 142,254, Apr. 21, 1980, abandoned.

[51] Int. Cl.⁴ ............................................. A61B 10/00
[52] U.S. Cl. ..................................... 128/758; 128/304
[58] Field of Search .............................. 128/757–759, 128/304, 749, 756; 604/22

[56] References Cited

U.S. PATENT DOCUMENTS

| Re. 27,915 | 2/1974 | Kohl | 128/757 |
|---|---|---|---|
| 2,471,088 | 5/1949 | Ayre | 128/757 |
| 3,088,454 | 5/1963 | Shute | 128/758 |
| 3,485,236 | 12/1969 | Frost | 128/757 |
| 3,592,186 | 7/1971 | Oster | 128/757 |
| 3,640,268 | 2/1972 | Davis | 128/757 X |
| 3,796,211 | 3/1974 | Kohl | 128/757 X |
| 3,877,464 | 4/1975 | Vermes | 128/759 |
| 4,016,865 | 4/1977 | Fredricks | 128/757 |

OTHER PUBLICATIONS

*Plastics Engineering Handbook* of the Society of the Plastics Industry, Inc., Third Edition, Reinhold Pub. Corp., New York (1960) pp. 297–299.

Primary Examiner—Edward M. Coven
Assistant Examiner—Max F. Hindenburg
Attorney, Agent, or Firm—Ward Brown; Robert W. Beach

[57] ABSTRACT

An elongated plastic aspirator tube has a proximate end portion adapted for quick connection to a suction-generating device, such as a rubber squeeze bulb or a syringe, for collection of cell-containing mucus from the uterine endocervical canal, and a flattened distal end portion forming a spatulate scraper for collecting cells exfoliated from the transformation zone of the uterine cervix. The spatulate scraper includes a frontal lobe through which the bore of the aspirator tube opens, an adjacent lateral lobe abuttable against the ring of the cervix projecting into the vagina for positively positioning the apertured distal end of the frontal lobe at approximately the external os and a concave transition portion forming a scraping edge joining and faired into the adjacent edges of the two lobes. In a simple "one step" procedure, mucus from the endocervical canal is aspirated into the tube and the entire circumferential extent of the transformation zone scraped by rotation of the tube for collection of freshly exfoliated cells to be deposited on the flat surface of a slide. A circumferential rib divides the barrel of the tube into a long straight handle portion having longitudinally extending ridges assuring a slip-free grip and a shorter cylindrical stem carrying the spatulate scraper for spreading the collected samples uniformly and thinly on the slide surface.

17 Claims, 24 Drawing Figures

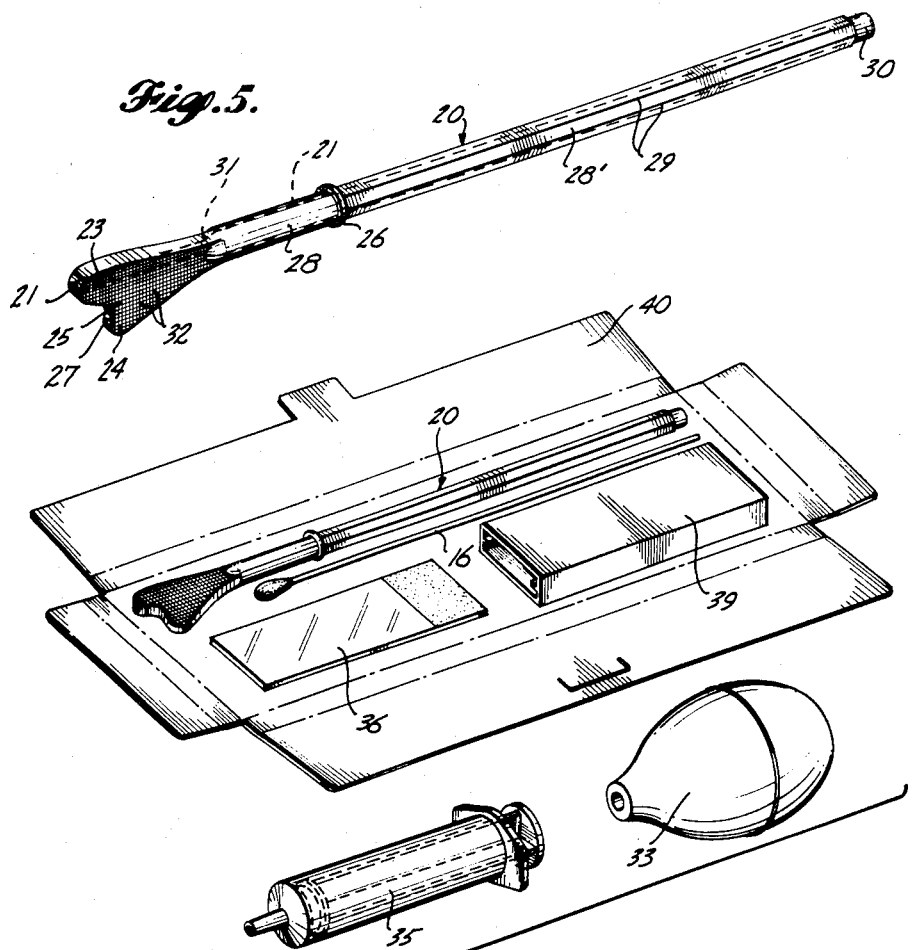
Fig. 5.
Fig. 6.
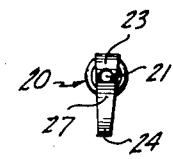
Fig. 8.
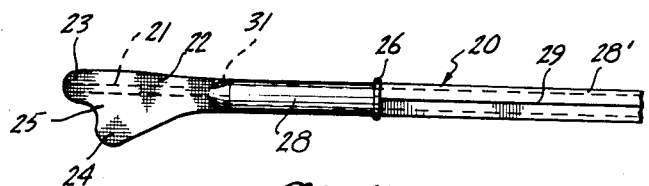
Fig. 7.

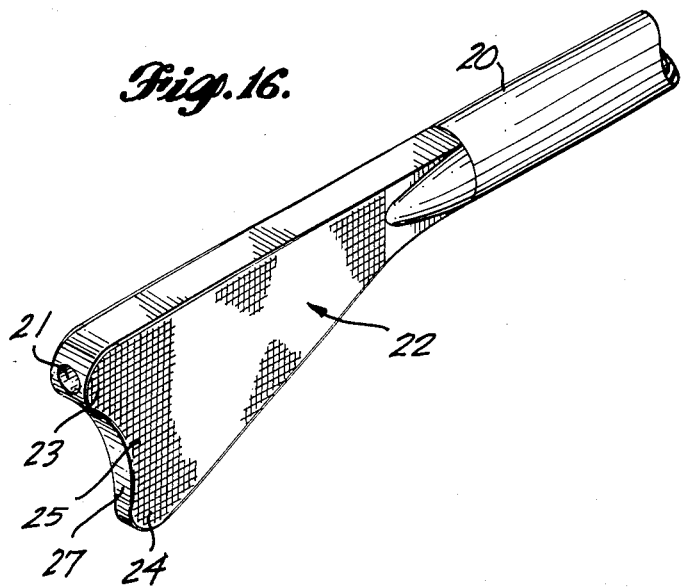
Fig.16.
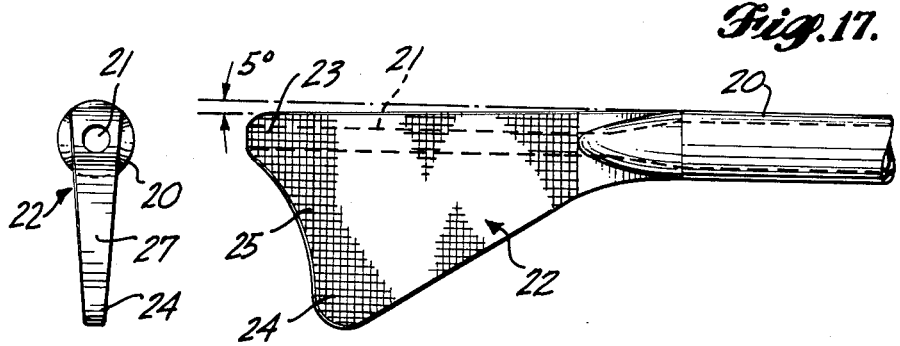
Fig.17.
Fig.18.
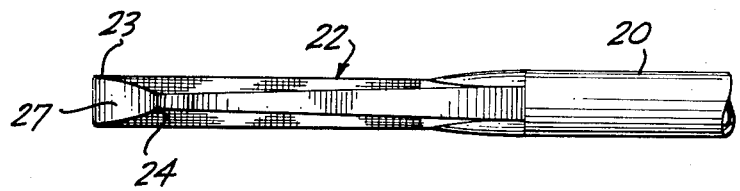
Fig.19.

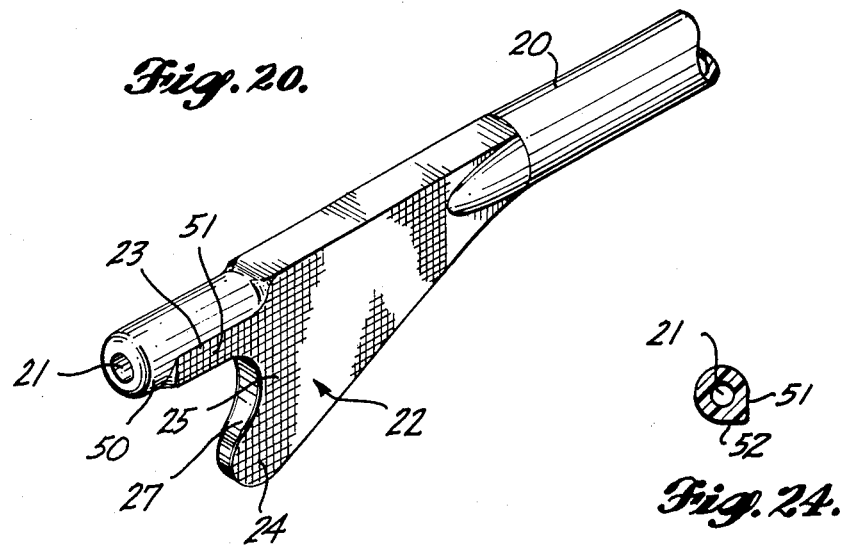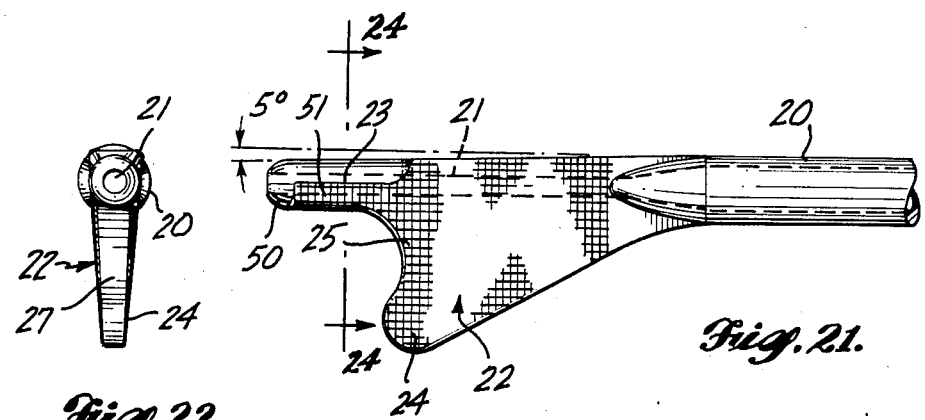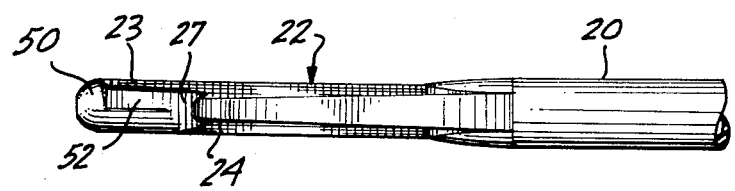

PAP SMEAR T-ZONE SAMPLER

CROSS-REFERENCE

This application is a continuation of application Ser. No. 405,783, filed Aug. 6, 1982, abandoned as of the filing date accorded to this application, which was a continuation-in-part of application Ser. No. 152,375, filed May 22, 1980, now abandoned which was a continuation-in-part of application Ser. No. 142,254, filed Apr. 21, 1980, now abandoned.

BACKGROUND OF THE INVENTION

1. Field of the Invention

The present invention relates to a cytological sampling instrument for collecting cells exfoliated from the uterine cervix.

2. Brief Description of the Prior Art Drawings

FIGS. 1, 2, 3 and 4 are corresponding, somewhat diagrammatic, generally axial sections through a vaginal cavity showing in elevation the most popular prior art cytological sampling instruments currently in use.

3. Prior Art

In each of the known cervical cytological sampling methods the object is to collect a large number of cells that originated at the uterine cervix and, to a lesser degree, at the uterus, to be deposited on a slide and "fixed" by application of fixative for preservation of the cells. After suitable processing, subsequent microscopic examination in a medical laboratory reveals whether or not abnormal cells are present which are indicative of cancer or lesions accepted as being precursors of cancer.

As illustrated in FIG. 1, in one method the vagina 1 is distended by a speculum 2 enabling the portio vaginalis (vaginal portion) 11 of the cervix to be viewed, and a paddle-like scraper 3 is used to collect exfoliated cells from the posterior fornix 4 of the vagina, that is, from the "vaginal pool". This is the area selected for sampling by Papanicolaou because cells exfoliated from virtually all areas of the cervix and from the uterus gather in the vaginal pool, though Papanicolaou proposed sampling this region by aspiration. Unfortunately, however, cells begin deteriorating immediately upon exfoliation to the point where at least a large proportion of the cells obtained in a vaginal pool smear have little or no diagnostic value. In addition, while large numbers of cells usually are obtained, the origins of the cells present in the vaginal pool at any given moment are not known so that there is no assurance that cells from areas prone to cancer will be obtained. It is now recognized that a false negative rate of about 50% can be expected for vaginal pool smears, that is, even after examination about one-half of the cases of invasive cervical cancer and cervical intraepithelial neoplasia ("CIN") remain undetected. Nevertheless, since vaginal pool smears are quickly, easily and inexpensively taken, they still are used to a large extent, particularly when funds for screening a large population are limited.

As early as 1947, the year in which the application resulting in Ayre U.S. Pat. No. 2,471,088 was filed, it was recognized that the vast majority of lesions resulting in invasive cervical cancer originate at the undulating circumferential border 5 between the squamous cells of the ectocervical epithelium 17 and the columnar cells of endocervical epithelium 18, which border is referred to as the squamo-columnar junction, the transformation zone or the "T-zone". Though the T-zone is variously located in different women, usually it is at or closely adjacent to the external os 6. It is extremely important that cells from this area be present in a sample.

Ayre invented the specially designed scraper 7 shown in FIG. 2 to be used for scraping the entire circumferential extent of the T-zone for early detection of cell abnormalities. In general, the Ayre scraper has two lobes including a frontal lobe 8 insertable slightly into the endocervical canal 9 and an adjacent lateral lobe 10 abuttable against the vaginal portion or ring 11 of the cervix. The frontal lobe 8 acts as a pivot as the scraper is rotated for scraping of the entire circumferential extent of the T-zone.

Ayre, himself, recognized that a more reliable diagnosis could be obtained if the scraping sample was not the only sample obtained from a patient. He proposed that at least two separate sampling operations be performed—one using his scraper and another using a separate instrument for obtaining an additional sample directly from the endocervical canal. In fact, research has shown that relying solely on a sample obtained by use of an Ayre scraper can result in a false negative rate of as high as about 30%.

Methods for obtaining samples directly from the endocervical canal are shown in FIGS. 3 and 4. In the method of FIG. 3, the narrow forward end of a pipette 13 is inserted into the endocervical canal. Preferably the tip of the pipette is positioned at about the external os, but it is difficult to position the pipette precisely so that sometimes the tip of the pipette is inserted almost up to the internal os 14 as shown in FIG. 3. Suction is applied drawing mucus containing exfoliated cells into the lumen of the pipette. Published research suggests that carefully performed external os aspiration gives more reliable results than any other known single method. A problem, however, is that the endocervical epithelium, unlike squamous epithelium, is friable and prone to bleeding. Not only is bleeding worrisome to the physician and patient, but a sample containing a substantial amount of blood cannot be evaluated by the cytologist with confidence. Another problem is that the method of FIG. 3 more often should be performed by a physician, whereas the methods of FIGS. 1 and 2 can be performed by skilled paramedic technicians.

In the method of FIG. 4 the soft tip 15 of a saline-moistened cotton-tipped applicator 16 is inserted into the endocervical canal and rotated and moved in and out. While less traumatic than the method of FIG. 3, there still is a chance of endocervical mucosal injury and bleeding. Also, cells valuable for diagnostic purposes adhere in the interstices of the cotton fiber. Further, it is difficult to transfer the sample to a slide, and vigorously rubbing the cotton-tipped applicator on the slide distorts the cells making them difficult to evaluate.

Adherence of and damage to cells also is a problem with the methods of FIGS. 1 and 2 because most scrappers presently used are manufactured from thin strips of wood and cells become trapped in the pores and cracks in the wood. There also is a possibility of abrading the cervix with the irregular edge of a wood scraper which may reduce the reliability of any future colposcopic examination of the cervix.

Two or more of the above conventional methods can be performed in sequence on each patient. Prior research has demonstrated that the combination of prior art methods resulting in the lowest false negative rate, a rate as low as 2%, is the combination of the methods of FIGS. 2 and 3, that is, the combination of T-zone scraping and external os aspiration. In spite of experts' recommendations that this combination of methods be used, physicians continue to use suboptimal methods, possibly because of the difficulty of performing an external os aspiration. For example, in a recent survey only 3.1% of pathologists representing 675 cytology laboratories stated that a combined external os aspiration and T-zone scraping sample was a "type of routine gynecologic smear" received by their laboratories.

A major problem in obtaining Pap smears is that any cells that are allowed to dry before being fixed become distorted and impossible to evaluate. Under ideal circumstances a sample is transferred to a slide and fixed almost immediately, within seconds after being obtained. This problem is magnified when a combination of prior art methods is used because usually all of the separate samples are obtained and placed on a slide before any sample is fixed, with the result that at least some air drying occurs.

Slides received at a laboratory show significant variation, illustrating a wide range of sampling techniques and methods of transfering collected cell-containing material to a slide. Individual slides may have a single large blop, multiple streaks, globs or a small spot of material such that it is difficult to examine individual cells, making examination time consuming and sometimes inaccurate.

In addition, a substantial proportion of slides received by a laboratory must be classified as "unsatisfactory" because no diagnosis can be given due to an inadequate amount of cell-containing material and/or significant air drying artifact. The proportion of "unsatisfactory" slides varies widely; for example, in one research study involving ten clinics using the same method, T-zone scraping, only one-half of 1% of the slides from one clinic had to be labeled unsatisfactory, whereas 25.6% of the slides from another clinic had to be labeled unsatisfactory because of an inadequate quantity of well defined cells. In this case, the patient should be scheduled for an additional smear sample to be taken which, in effect, doubles the inconvenience to the patient, the work of the doctor or paramedic and the consequent expense. Also, the patient may be distressed from having been asked to return for an additional smear, regardless of the reassurances that she receives from the physician that an abnormality is unlikely.

Different instruments and methods have been proposed to solve one or more of the problems discussed above. For example, to reduce expense it has been proposed that a sample be obtained by the patient herself, such as by use of a specially designed tampon or a "vaginal irrigation" kit, and mailed directly to the medical laboratory. High false negative rates have been demonstrated for self-obtained samples and, accordingly, use of these methods has been discouraged.

One study, in an attempt to explain the high false negative rate when screening for cervical intraepithelial neoplasia, verified that high numbers of cells are trapped in cotton-tipped applicators and wooden scrapers, whereas relatively few cells are trapped in plastic instruments; yet use of plastic instruments has been discouraged because such instruments have been manufactured with thin scrapers having sharp edges that can lacerate or abrade the cervix.

Kohl in his U.S. Pat. No. Re. 27,915 disclosed a scraping instrument having a narrow, cylindrical aspiration pipette projecting forward from the scraping edge of the instrument for insertion into the endocervical canal. As the narrow projecting end of the pipette is inserted into the endocervical canal, the scraper and pipette pivot about a flexible shock-absorbing joint to align the axis of the pipette with the length of the canal. It still would be difficult to position the leading end of the Kohl pipette precisely, and for any patient whose T-zone is located at or inward of the external os, no T-zone scraping sample would be obtained because the T-zone, or part of it, would be engaged by only the smooth, cylindrical periphery of the aspiration pipette.

SUMMARY OF THE INVENTION

The principal object of the present invention is to provide a sampling instrument for obtaining cell-containing material from the uterine cervix, and a safe, reliable method for use of such instrument that can be performed quickly and easily by a physician or paramedic technician and that results in uniform samples of high diagnostic quality that can be examined quickly and inexpensively by a cytologist.

In the present invention, the foregoing object is accomplished by each of several embodiments of a horizontally elongated aspirator tube having a flattened distal end portion forming a spatulate scraper including a frontal lobe through which the bore of the tube extends. An adjacent downward projecting lateral lobe is abuttable against the vaginal ring of the cervix for positioning the apertured tip of the tube at approximately the external os. A concave transition section of the scraper extends between the two lobes and is shaped substantially complementally to the inner margin of the vaginal ring of the cervix.

Preferably, a blunt scraping edge extends between the opposite lateral sides of the scraper. Such scraping edge forms the distal or leading edge of the lateral lobe, then curves forward to form the outer edge of the concave transition section and then extends a substantial distance forward to form the outer or bottom edge of the frontal lobe. The margin of a lateral side of the scraper adjacent to the scraping edge is planar, and a substantially angular but slightly rounded junction is formed between the scraping edge and such planar margin.

The flat scraping edge can extend all the way forward up to a broad and blunt aperture tip of the tube, or such edge can stop short of the tube opening so that the distal tip portion of the tube can be cylindrical. In either case, the scraping edge and the substantially angular junction between such edge and the planar lateral margin of the scraper can extend forward sufficiently so as to engage a T-zone located at or inward of the external os.

Preferably, the lateral lobe of the scraper decreases in thickness outward from the aspirator tube bore so that the sampler can be molded of plastic material without any substantial "dishes" being formed in its opposite lateral sides. The lateral and frontal lobes also can decrease in thickness forward, though the edges of the lobes still should be blunt.

A second scraping edge can be provided at the top of the instrument for obtaining a sample for hormonal evaluation, such as from the lateral vaginal wall. Since such wall is less delicate than the endocervix, the junction between the second scraping edge and the planar lateral side of the scraper can be sharper than the junction adjacent to the first scraping edge. In use, suction is applied to the proximate end portion of the aspirator tube for drawing cell-containing mucus into the tube from the external os area. At the same time, or subsequently, the sampler is rotated for scraping the entire circumferential extent of the T-zone. The aspiration sample is pooled onto a slide and the flat lateral side of the scraper is rubbed gently in the pool for transferring the scraping sample onto the slide. The combined sample is spread thinly and evenly substantially as a monolayer of cells on the slide surface and suitable fixative is applied immediately.

BRIEF DESCRIPTION OF THE DRAWINGS OF THE PREFERRED EMBODIMENTS

FIG. 5 is a top perspective of a Pap smear T-zone sampler in accordance with the present invention.

FIG. 6 is a top perspective of a kit including the sampler of FIG. 5, a cotton-tipped applicator, a glass slide, a protective slide case and a package for those components, as well as alternative suction-generating devices for use with the sampler.

FIG. 7 is a fragmentary side elevation of the distal end portion of the sampler of FIG. 5 and FIG. 8 is an end elevation of the sampler of FIG. 5.

Figure 1:
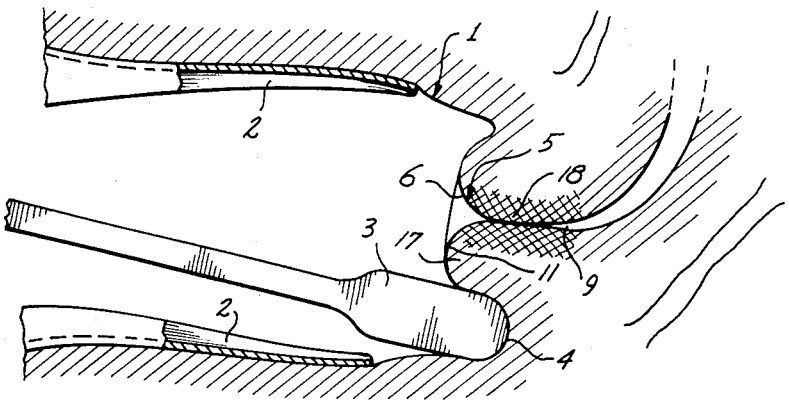
Figure 2:
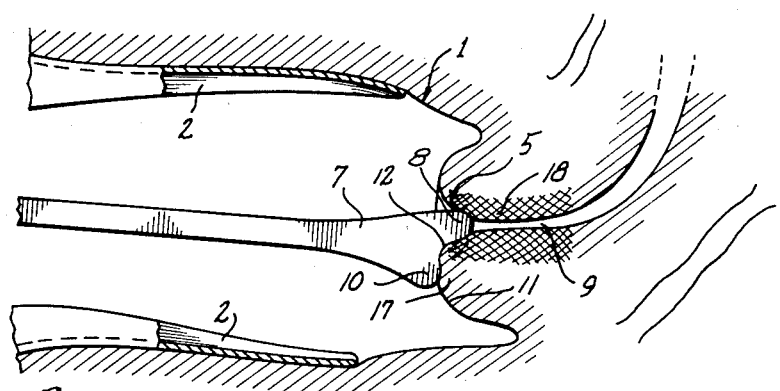
Figure 3:
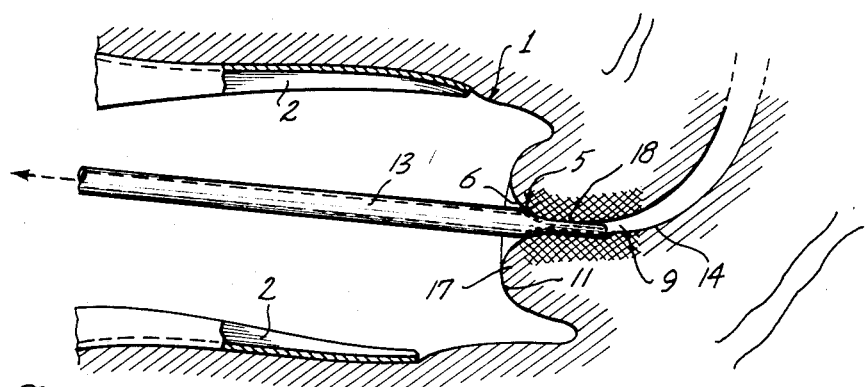
Figure 4:
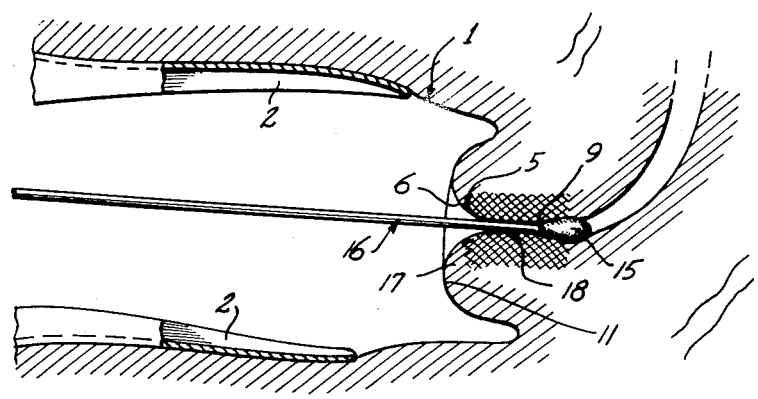
Figure 9:
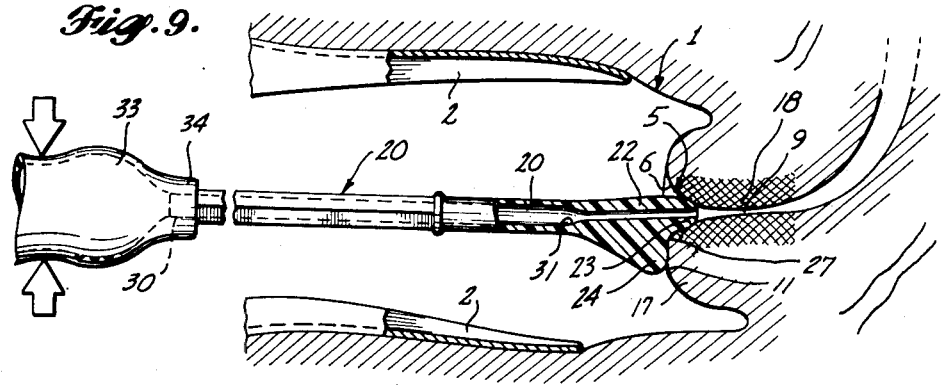
Figure 10:
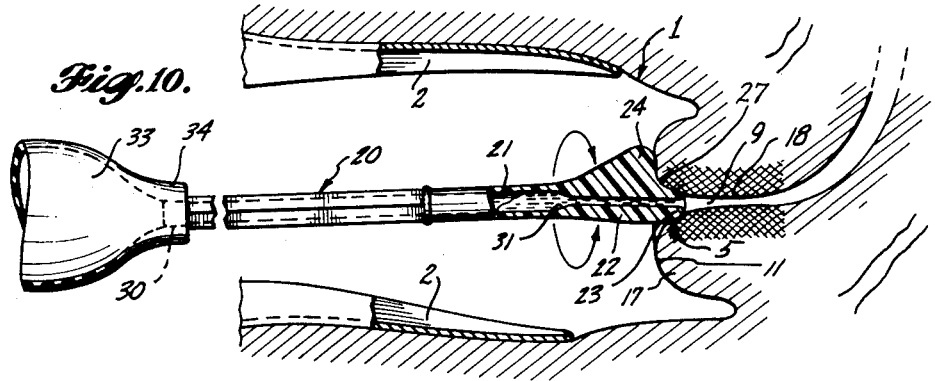

FIGS. 9 and 10 are corresponding, somewhat diagrammatic, generally axial sections of a vaginal cavity illustrating a sampler in accordance with the present invention being used for collecting a sample of cell-containing material, with parts broken away, and FIGS. 11, 12, 13 and 14 are corresponding, fragmentary, somewhat diagrammatic, top perspective illustrating the sample being deposited on a glass slide and fixed.

Figure 15:
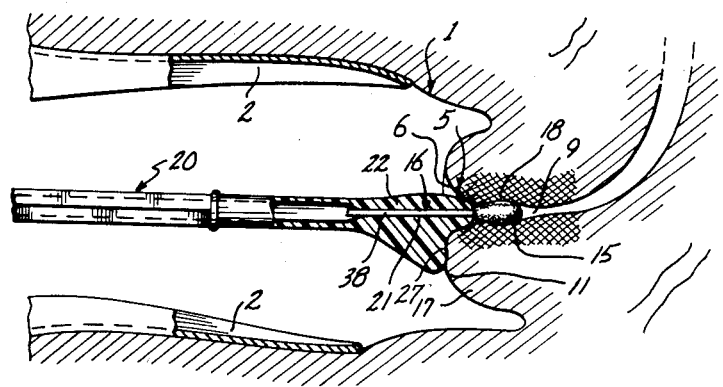

FIG. 15 is a somewhat diagrammatic, generally axial section through a vaginal cavity illustrating an alternative manner of collecting a sample by use of the Pap smear T-zone sampler of FIG. 5, with parts broken away, FIG. 16 is a fragmentary top perspective of the distal end portion of a second embodiment of a pap smear T-zone sampler in accordance with the present invention;

FIG. 17 is a side elevation thereof;

FIG. 18 is an end elevation thereof; and

FIG. 19 is a bottom plan thereof.

FIG. 20 is a fragmentary top perspective of the distal end portion of a third embodiment of a paper smear T-zone sampler in accordance with the present invention;

FIG. 21 is a side elevation thereof;

FIG. 22 is an end elevation thereof;

FIG. 23 is a bottom plan thereof; and

FIG. 24 is a vertical section taken along lines 24—24 of FIG. 21.

DETAILED DESCRIPTION OF THE PREFERRED EMBODIMENTS

The embodiment of the present invention shown in FIG. 5 includes a horizontally elongated aspirator tube 20 having a substantially linear axial through bore 21. The distal end portion 22 of the tube is flattened forming a spatulate scraper having a blunt nosed, forward projecting or frontal lobe 23 and an adjacent downward projecting or lateral lobe 24. A concave transition section 25 of the scraper is faired into the adjacent edges of the two lobes.

At least one and preferably both of the opposite upright lateral sides of the scraper are planar. A blunt scraping edge 27 having linear horizontal elements of substantial length extends between such opposite lateral sides and forms the leading edge of the lateral lobe 24, the outer edge of the concave transition section 25 and the outer or bottom edge of the frontal lobe 23. The leading portion of the scraping edge extends forward generally parallel to the axis of the tube bore and then is curved upward to the opening of the bore. The corners forming junctions between the opposite lateral sides of the scraper and its flat scraping edge are substantially angular but, nevertheless, slightly rounded.

A circumferential rib 26 divides the long barrel of the tube into a cylindrical stem 28 carrying the spatulate scraper and a long straight handle portion 28'. Such handle portion is of hexagonal cross section, forming longitudinally extending grip-promoting ridges 29. The relatively short proximate end portion 30 of the tube is cylindrical.

The bore 21 of the tube opens at about the center of the blunt convexly rounded tip of the scraper frontal lobe 23. Throughout the length of the scraper portion 22, such bore is of uniform, but small, diameter. Proceeding toward the proximate end of the tube, the diameter of the bore increases abruptly forming an annular step 31. Throughout the length of the barrel of the tube, the diameter of the bore is uniform, but large in comparison to the diameter of the distal portion of the bore extending through the spatulate scraper.

It is preferred that the aspirator tube be injection molded from plastic material. However, injection molded plastic material has a tendency to shrink in the center of a large thick area forming a characteristic depression or "dish". By tapering the spatulate scraper from top to bottom, that is, by gradually and uniformly decreasing the thickness of the scraper outward toward the tip of the lateral lobe, as shown in FIG. 8, shrinking of the plastic material at the center of the lateral lobe is less of a problem and both sides of the scraper will be substantially planar rather than having substantial central depressions.

Preferably the planar side faces of the scraper are slightly hydrophilic, which can be achieved by adding a hydrophilic substance to the plastic material from which the scraper is formed or, as shown in the drawings, by texturing such sides by molding short crisscrossed ribs 32 integrally in the sides of the scraper as best seen in FIG. 5.

As shown in FIGS. 9 and 10, in a simple "one-step" operation involving only a single insertion of the Pap smear T-zone sampler of the present invention into the vagina, both an external os endocervical aspiration sample and a T-zone scraping sample can be obtained. The sampler is inserted lengthwise into the vagina 1 distended by a conventional speculum 2 and the broad rounded tip of the frontal lobe 23 is substantially self-centering in the endocervical canal 9 without fear of lacerating or puncturing the cervix. The leading edge of the scraper lateral lobe 24 is located for engagement with the vaginal ring 11 of the cervix to position the apertured tip of the frontal lobe slightly inward of the external os 6. The scraping edge 27 of the scraper is in engagement with the inner margin of the vaginal ring 11 of the cervix and extends inward past the T-zone 5.

Suction is applied to the tube at its proximate end portion, such as by use of a rubber squeeze bulb 33 having its apertured tip 34 snugly fitted over the cylindrical proximate end portion 29 of the tube in sealing engagement. Alternatively, the flared, distal, lumen-forming end portion of a conventional syringe, such as the syringe 35 shown in FIG. 7, can be fitted inside the bore of the cylindrical proximate end portion of the tube so that the syringe can be used as a suction-generating device. In either case, the suction is concentrated in the endocervical canal because the distal end portion of the tube bore is of small diameter. Even viscous cell-containing mucus will be drawn into the tube.

While the aspirator tube itself is disposable after use, preferably the suction-generating device is reusable and, accordingly, it is preferred that no mucus be drawn into the suction-generating device so as to contaminate future samples. Since the tube bore is of large diameter in the barrel of the tube, a substantial amount of mucus can be drawn into the tube without entering the suction-generating device. In addition, the abrupt step 31 of the bore causes a turbulent flow tending to retain the mucus in the distal end portion of the tube bore, as opposed to a laminar flow which could result in mucus flowing horizontally into the suction-generating device.

After the aspiration sample has been drawn into the tube, the tube is rotated as the scraping edge 27 of the spatulate scraper is held gently against the inner margin of the cervix. The substantially angular but slightly rounded junction between the scraping edge and the leading lateral side of the scraper facilitates collection of freshly exfoliated cells on such leading lateral side. The entire circumferential extent of the T-zone is scraped by at least one full rotation of the scraper. The scraping sample adheres to the leading lateral side of the scraper because the sides of the scraper are textured or slightly hydrophilic.

An alternative to the two sequential sample-collecting steps described above is to obtain the aspiration sample as the scraper is being rotated, in which case cell-containing material accumulating at the rotating leading side of the scraper may be drawn into the tube bore with mucus from the endocervical canal. Another alternative is to rotate the tube for obtaining the scraping sample first, followed by withdrawing the tube slightly and then applying suction for obtaining the aspiration sample so that exfoliated cells from the T-zone that did not adhere to the leading side of the scraper will be drawn into the tube bore.

Figure 11:
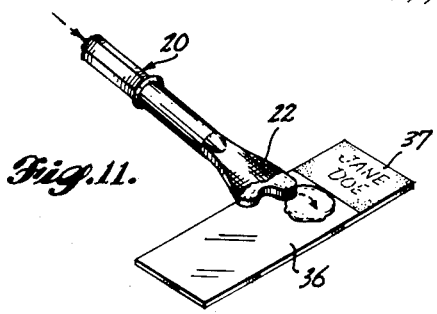
Figure 12:
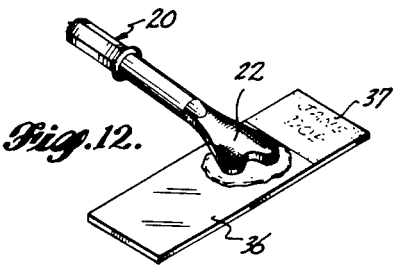
Figure 13:
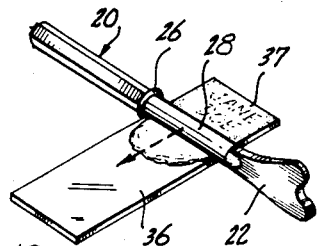
Figure 14:
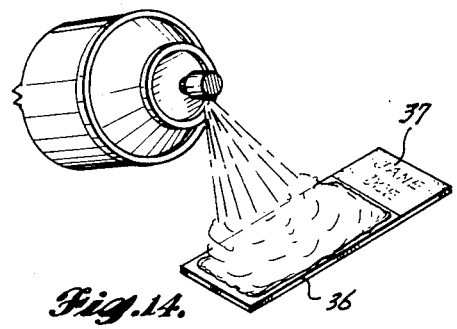

Regardless of the sample-collecting method that is used, in rapid sequence the aspirated sample and the scraped sample are deposited on a glass slide 36 and fixed, as shown in FIGS. 11 through 14. As indicated in FIG. 11, first the aspiration sample is pooled onto the slide immediately adjacent to its frosted end 37. Next the scraped sample is transferred to the slide by gently rubbing the leading side of the scraper in the pool as illustrated in FIG. 12. Since such side is planar, it can be laid flat against the slide assuring that substantially all cells will be transferred. The combined sample can be spread substantially uniformly and thinly on the upper surface of the slide, as illustrated in FIG. 13, by butting the circumferential rib 26 of the tube against a longitudinal edge of the slide with the cylindrical sample-spreading stem 28 resting flatly on the upper surface of the slide and moving the tube lengthwise of the slide away from its frosted end. Immediately following spreading of the sample, the sample is fixed such as by use of a conventional spray-type fixative as illustrated in FIG. 14.

The entire sample transferring and fixing operation can be performed in a matter of a few seconds so that there will be no appreciable air drying of either sample. Each slide should have a thin layer of well preserved cells, making microscopic examination and diagnosis quick and reliable.

While the combination of external os aspiration and T-zone scraping is the most reliable sampling method for detecting the presence of abnormal cells, in some women there simply is not enough mucus at the external os that an aspiration sample can be obtained. The so-called "dry cervix" is particularly prevalent in peri- or post-menopausal women. Nevertheless, as illustrated in FIG. 18, the Pap smear T-zone sampler of the present invention still can be used in a simple one-step operation for obtaining samples of exfoliated cells both from the endocervical canal and the T-zone, even from a woman having a "dry cervix".

As shown in FIG. 15, the shaft 38 of a cotton-tipped applicator 16 can be inserted into the narrow distal end portion of the bore 21 of the tube 20 up to the soft tip 15 of the applicator. Preferably the diameter of the tube bore is only slightly greater than the diameter of the shaft so that the cotton-tipped applicator is received in the tube bore in snug engagement for firmly connecting the applicator to the aspirator tube.

In use, the aspirator tube still is substantially self-centering as it is inserted lengthwise into the vagina 1 for inserting the tip of the cotton-tipped applicator into the endocervical canal 9. When fully inserted, the scraping edge 27 of the flattened spatulate scraper portion 22 of the tube is in engagement with the T-zone 5. As the tube is rotated for obtaining a T-zone scraping sample, simultaneously exfoliated cells in the endocervical canal are collected on the tip of the cotton tipped applicator. After at least one full revolution, the tube is withdrawn and, quickly, the cotton-tipped applicator and the leading side of the scraper are rubbed gently against a glass slide for transferring cellular material to the slide. The combined samples are fixed immediately.

The present invention also can be used for obtaining a sample for hormonal evaluation, which sample preferably is obtained from the proximal third of the lateral vaginal wall. For example, following the sample obtaining, transferring and fixing operation described with reference to FIGS. 9 through 14 or FIG. 15, the top edge of the scraper opposite its lateral lobe can be rubbed gently against the lateral vaginal wall between the blades of the speculum. This sample from the lateral vaginal wall can be deposited on a separate slide or at one end portion of the slide containing the cervical scrape sample.

As illustrated in FIG. 6, the present invention can be provided in a kit including: the Pap smear T-zone sampler 20 of the present invention, which usually will be used to obtain an external os aspiration sample and T-zone scraping sample as shown in FIGS. 9 and 10; a long shafted cotton-tipped applicator 16, which can be used for wiping away excess mucus from the vaginal portion of the cervix or which can have its shaft shortened for insertion into the bore of the sampler as illustrated in FIG. 15; a slide 36 for receiving a sample taken by use of the sampler of the present invention; a rigid slide case 39 for protecting the slide in a transit to a medical laboratory; and a folding cardboard package 40 which may be of the return mailer type. Also required for use of the present invention is a suctiongenerating device; either a 50 cc rubber squeeze bulb 33 or a 20 cc plastic syringe 35 can be provided separately. Similarly, spray fixative is preferred and also can be provided separately.

With respect to the preferred dimensions for the embodiment described above, to assure adequate suction by use of a 50 cc rubber squeeze bulb or a 20 cc syringe the diameter of the narrow distal end portion of the tube bore should be no greater than about ⅛ inch (0.32 cm). As discussed above, preferably the diameter of the narrow portion of the bore is substantially the same as the diameter of the shaft of a cotton-tipped applicator which, for applicators currently available, is about 3/32 inch (0.24 cm). the diameter of the larger proximate end portion of the bore should be at least about 1½ times, preferably about 2 times, the diameter of the narrow distal end portion of the bore for creating the abrupt step between the two bore portions and for storing a substantial quantity of mucus.

The transverse thickness of the spatulate scraper should be small, preferably no greater than about twice the diameter of the narrow portion of the tube bore, because there is less chance of a "dish" resulting in a thin section of injection molded plastic material than in a thicker section. Nevertheless, the scraper must be thick enough that the lateral walls of the tube bore will not break or bend appreciably during use of the instrument. In the embodiment described above, the scraper is tapered uniformly from its thickest top portion, which is about 3/16 inch (0.48 cm) thick, to its thinnest bottom portion, which is about 3/32 inch (0.24 cm) thick, as shown in FIG. 8.

The upright height or width of the frontal lobe is large in comparison to the diameter of the narrow portion of the tube bore to eliminate the possibility of perforating the cervix. Preferably the width of such lobe, that is, the upright dimension as shown in FIG. 7, is at least twice the diameter of the narrow portion of the tube bore, in the preferred embodiment about ¼ inch (0.64 cm) which is between 2 and 3 times the preferred bore diameter. In addition, the tip of the frontal lobe is blunt and rounded, having a radius of curvature at least equal to about the diameter of the narrow portion of the tube bore. In the embodiment described above, the tip of the frontal lobe is substantially semicircular, the radius of curvature being about ⅛ inch (0.32 cm).

The leading edge of the lateral lobe must project laterally outward a distance sufficient for engagement with the vaginal ring of the cervix and in the embodiment described above such lobe projects outward about 7/16 inch (1.1 cm) from the axis of the tube bore. In addition, such leading edge must be located rearward from the apertured tip of the frontal lobe a distance such that the apertured tip of the frontal lobe is in close proximity to the external os when the leading edge of the lateral lobe is in engagement with the vaginal ring of the cervix. In the preferred embodiment, the leading edge of the lateral lobe is located rearward of the tip of the front lobe a distance approximately equal to the width of the front lobe, that is, approximately ¼ inch (0.64 cm).

The substantially angular corners forming junctions between the scraper lateral side faces and the T-zone scraping edge must be rounded sufficiently as to prevent abrading the cervix yet should not be so rounded as to prevent a good scraping effect for collecting exfoliated cells. Preferably the radius of curvature of each of such corners is about 0.01 inch (0.25 mm), and should be no greater than about 0.03 inch (0.76 mm). The top edge of the scraper, which may be used to obtain a sample from the lateral vaginal wall, can have somewhat sharper longitudinally extending corners because the vaginal wall is less friable and prone to bleeding than the cervix. Preferably the radius of curvature of each upper longitudinally extending corner is about 0.001 inch (0.025 mm) or less.

With respect to the cylindrical proximate end portion of the tube, the outside diameter and the length of such end portion must be sufficient for firm sealing engagement in the aperture of a conventional 50 cc rubber squeeze bulb. In the preferred embodiment, the outside diameter of the proximate end portion is about ¼ inch (0.64 cm) and such end portion is about 11/32 inch (0.87 cm) long. Similarly, the inside diameter of the proximate end portion must be such as to fit over the distal, lumen-forming tip of a conventional 20 cc syringe in snug sealing engagement. A diameter of about 5/32 or 3/16 inch (0.40 or 0.48 cm) for the distal end portion of the tube bore meets this requirement.

Finally the length and diameter of the long straight handle portion of the tube should be sufficient that the tube can be manipulated easily. In the preferred embodiment, the barrel of the tube is about 6 inches (15 cm) long and the distance between opposite flat sides of the handle portion is slightly greater than ¼ inch (0.64 cm) such that the handle portion is about the same size and is the same shape as a pencil, assuring easy handling of the instrument.

The sampler can be injection molded from clear polypropylene plastics material, in which case the sampler is sufficiently inexpensive that it can be thrown away after use.

Although there is substantial variation in the sizes of the cervices of different women and in the locations of the T-zones, the embodiment of the present invention described above can be used to obtain high-quality, reliable aspiration and T-zone scraping samples from at least a majority of women. Nevertheless, there are two situations in which a modification in the shape of the spatulate scraper portion of the sampler may be desirable, the first of which is the situation where the vaginal portion of the cervix is large and the T-zone is located a substantial distance outward of the external os. In a younger woman, for example, often the physician or paramedic technician can see the T-zone on the vaginal portion of the cervix and if such vaginal portion is large there is only a gradual curvature in the area of the T-zone. It may be difficult to obtain a good T-zone scraping sample by use of the first-described embodiment of the present invention because substantial forward force would have to be exerted to assure that the full axial extent of the T-zone is engaged by the scraping edge of the sampler. In addition, with the T-zone engaged by the scraping edge the frontal lobe may not be centered in the cervical opening.

The embodiment of the present invention shown in FIGS. 16 through 19 is modified to accommodate the condition discussed above. The proximate end portion, the handle and the sample-spreading stem are identical to the corresponding parts of the previously described embodiment, and the distal end portion of the horizontally elongated aspirator tube 20 still is flattened to form a spatulate scraper 22 having a frontal lobe 23, a downward projecting lateral lobe 24 and a concave transition section 256 joining the two lobes. The radius of curvature of the concave transition section for the embodiment of FIGS. 16 through 19, however, is substantially greater than the radius of curvature of the transition section of the first-described embodiment of the invention to approximate the curvature of the inner margin of the vaginal portion of the larger cervix. The scraping edge 27 of the scraper forming the leading edge of the lateral lobe 24, the outer edge of the concave transition section 25 and the bottom edge of the frontal lobe 23 still extends forward up to the opening of the aspirator tube bore 21 and still extends between planar opposite upright sides of the scraper forming therewith the substantially angular but slightly rounded junctions facilitating a thorough scraping of the T-zone.

Not only is the scraper tapered downward toward the tip of the lateral lobe 24 as in the previously described embodiment, it also is tapered forward as best seen in FIG. 19. The plane of each opposite lateral side of the scraper is not parallel to the axis of the tube bore but rather is somewhat oblique. The forward taper reduces the overall bulk of the scraper and makes the scraping edge 27 somewhat narrower, particularly toward the lower or outer tip portion of the lateral lobe.

As best seen in FIG. 17, the top longitudinal edge of the scraper is generally planar but is not precisely parallel to the axis of the tube bore. The top longitudinal edge slopes forward toward the tube bore at a small acute angle, preferably about 5 degrees, so that the thickness of the upper wall of the aspirator tube decreases gradually toward the forward tip of the frontal lobe 23. This taper decreases the overall size of the frontal lobe as compared to the tip of the previously described embodiment.

In other respects, the embodiment of the present invention shown in FIGS. 16 through 19 is the same as the embodiment shown in FIGS. 5 through 15, and it is used in the same manner.

The second situation in which modifications are desired in the first-described embodiment of the present invention is the situation where the T-zone is located at or inward of the external os and the cervix is quite small. In an older woman, for example, usually the T-zone cannot be viewed by the physician or paramedic technician, and in a post-menopausal woman the diameter of the cervical opening may be so small that insertion of a broad, blunt-nosed instrument is difficult and/or uncomfortable.

In the embodiment of the present invention shown in FIGS. 20 through 24, the distal tip portion 50 of the aspirator tube 20 is generally cylindrical and of reduced diameter as compared to the broader tips of the previously described embodiments so that such tip portion 50 can be inserted into the smaller cervix easily and without substantial discomfort. Rearward of such distal tip portion the aspirator tube still is flattened so as to form the spatulate scraper 22 having the downward-projecting lateral lobe 24, the frontal "lobe" 23 and the concave transition section 25 joining such lobes. As best seen in FIGS. 22 and 23, in general the opposite upright sides of the scraper are planar and the scraper is tapered both outward toward the tip of the lateral lobe and forward toward its distal end portion. As in the embodiment shown in FIGS. 15 through 19, in side elevation the upper longitudinal edge of the scraper is linear though sloped downward at a small angle, such as 5 degrees, relative to the axis of the tube bore. Accordingly, the thickness of the upper wall of the aspirator tube decreases toward the bore opening which aids in reducing the overall size of the distal tip of the instrument.

The radius of curvature of the concave transition section 25 of the embodiment of FIGS. 20 through 23 is substantially smaller than for the previously described embodiments. Such transition section forms a depression extending proximally behind the forward tip of the lateral lobe 24 so as to cup the vaginal portion of a smaller cervix. Preferably such leading tip of the lateral lobe is located about ⅜ inch (9.5 mm) behind the apertured distal tip of the aspirator tube. The blunt scraping edge 27, forming the leading edge of the lateral lobe, the outer edge of the concave transition section and, as described further below, the bottom edge of the frontal lobe, extends generally between the opposite upright lateral sides of the scraper in the area of the lateral lobe and the transition section, forming substantially angular but slightly rounded scraping junctions with the planar upright sides of the scraper.

In the area of the frontal lobe 23, however, only one of the opposite sides of the scraper has a marginal portion 51 coplanar with the corresponding scraper side. Such marginal portion forms a substantially angular but slightly rounded junction with a narrow, flat portion 52 of the scraping edge 27 projecting a substantial distance forward generally parallel to the axis of the tube bore. Such edge extends inward from such upright side to the midline of the aspirator tube, as shown in FIGS. 23, with the remainder of the frontal lobe being cylindrical as best seen in FIG. 24. Upon insertion of the instrument, the T-zone located at or inward of the external os of the smaller cervix is engaged by the single substantially angular junction between the planar margin 51 of the frontal lobe and the narrow, forward-projecting, blunt scraping edge. The instrument should be rotated only clockwise so as to scrape the entire circumferential extent of the T-zone to collect freshly exfoliated cells on the planar margin 51 of the frontal lobe.

As best seen in FIG. 20, the leading tip portion of the planar margin 51 is faired into the cylindrical distal tip portion 50 of the aspirator tube 20 so that there is no sharp point which could lacerate or abrade the endocervix as the instrument is inserted. Nevertheless, due to the lack of a blunt-nosed, convexly rounded, distal tip portion of the frontal lobe, more care must be taken when inserting the smaller cylindrical distal tip portion of the instrument into the cervix than with the previously described embodiments.

In other respects the embodiment of FIGS. 20 through 24 is identical to the first-described embodiment.

As noted above, in at least most cases the first-described embodiment of the present invention can be used to obtain a high-quality, reliable sample without undue discomfort. Nevertheless, the nature of an individual physician's practice may require more frequent use of one of the alternative embodiments having the changes noted above, such as if a very large proportion of the physician's patients are post-menopausal or adolescent women.

I claim:

1. A sampling instrument for collecting cells exfoliated from the uterine cervix of a woman and having a horizontally elongated aspirator tube with respective proximate and distal ends, the distal end portion of the tube being insertable into the aperture of the cervix and having a portion flattened to form a lateral lobe projecting downward transversely of the length of the tube for engagement against the vaginal ring of the cervix, the tube having a through bore enabling mucus in the endocervical canal to be sucked into such bore, characterized by the flattened portion of the distal end portion of the tube forming a scraper having the combination of: a flattened frontal lobe including a blunt-nosed, convexly rounded distal tip portion insertable into the aperture of the cervix, the tube bore opening substantially at the periphery of said blunt-nosed, convexly rounded distal tip portion, and said frontal lobe projecting forward from the lateral lobe a distance sufficient to position said bore opening at approximately the external os when the lateral lobe is in engagement with the vaginal ring of the cervix; a concave transition section disposed between and joining the upper portion of the lateral lobe and the proximate portion of said frontal lobe; a blunt scraping edge engageable with the inner margin of the vaginal ring of the cervix and positioned to extend across the area of the transformation zone when the lateral lobe is engaged against the vaginal ring of the cervix, said blunt scraping edge forming the distal edge of the lateral lobe, the outer edge of said transition section and the bottom edge of said frontal lobe; and at least one substantially planar upright lateral side offset from the tube bore and forming with said scraping edge an angular junction enabling collection of a scraping sample of exfoliated cells from the transformation zone while the distal tip portion of the tube is inserted for collection of an aspiration sample.

2. An instrument as claimed in claim 1, in which the radius of curvature of the periphery of the distal tip portion of the frontal lobe is at least as great as the diameter of the bore opening such that the upright height of the frontal lobe is at least twice the diameter of the bore opening.

3. An instrument as claimed in claim 1, in which the blunt-nosed, convexly rounded distal tip portion of the frontal lobe is substantially semicircular in profile and the tube bore opens substantially centrally of the blunt-nosed distal tip portion of the frontal lobe.

4. An instrument as claimed in claim 1, in which the periphery of the distal tip portion of the frontal lobe extends generally radially from the bore opening substantial distances in opposite directions for forming the blunt-nosed distal tip portion.

5. An instrument as claimed in claim 1, in which the minimum horizontal thickness of the scraper in a direction laterally of the tube bore is at least as great as the diameter of the bore opening.

6. An instrument as claimed in claim 1, in which the scraper has a second longitudinally extending scraping edge forming an upper edge portion of the scraper for scraping a sample from a lateral wall of the vagina.

7. An instrument as claimed in claim 6, in which the junction between the substantially planar lateral side of the scraper and the second scraping edge is sharper than the junction between such lateral side and the primary scraping edge.

8. An instrument as claimed in claim 1, in which the primary scraping edge includes a forward projecting portion extending distally longitudinally of the tube bore a substantial distance and forming the bottom edge of the frontal lobe, and the substantially planar upright side of the scraper includes a marginal portion adjacent to said forward projecting portion of the primary scraping edge and forming therewith a substantially angular junction facilitating scraping of exfoliated cells.

9. A sampling instrument for collecting cells exfoliated from the uterine cervix of a woman and having a horizontally elongated aspirator tube with respective proximate and distal ends, the distal end portion of the tube being insertable into the aperture of the cervix and having a portion flattened to form a lateral lobe projecting downward transversely of the length of the tube for engagement against the vaginal ring of the cervix, the tube having a through bore enabling mucus in the endocervical canal to be sucked into such bore, characterized by the flattened portion of the distal end portion of the tube forming a scraper having the combination of: a frontal lobe insertable into the aperture of the cervix, said frontal lobe projecting forward from the lateral lobe a distance sufficient to position said bore opening at approximately the external os when the lateral lobe is in engagement with the vaginal ring of the cervix; a concave transition section disposed between and joining the upper portion of the lateral lobe and the proximate portion of said frontal lobe; a blunt scraping edge engageable with the inner margin of the vaginal ring of the cervix and including a forward projecting portion extending distally generally longitudinally of the tube a substantial distance, said scraping edge being positioned to extend across the area of the transformation zone when the lateral lobe is engaged against the vaginal ring of the cervix and forming the distal edge of the lateral lobe, the outer edge of said transition section and the bottom edge of said frontal lobe; and at least one substantially planar upright lateral side offset from the tube bore, extending along the entire length of said scraping edge and forming therewith an abrupt junction enabling collection of exfoliated cells from the transformation zone while the distal tip portion of the tube is inserted for collection of an aspiration sample.

10. An instrument as claimed in claim 9, in which the tube is substantially rigid molded plastic material and the scraper is tapered downward in the direction of projection of the lateral lobe, the scraper decreasing in horizontal thickness from the tube bore toward the tip of the lateral lobe.

11. An instrument as claimed in claim 9, in which the junction between the primary scraping edge of the scraper and the substantially planar lateral side of the scraper is slightly rounded.

12. An instrument as claimed in claim 11, in which the radius of curvature of the junction between the primary scraping edge of the scraper and the substantially planar lateral side of the scraper is between about 0.01 inch (0.25 mm) and about 0.03 inch (0.76 mm).

13. An instrument as claimed in claim 9, in which the scraper includes a substantially semi-cylindrical side located opposite the substantially planar side.

14. An instrument as claimed in claim 9, in which the scraper has a substantially cylindrical distal tip portion and a scraping angular corner projection projecting laterally from said substantially cylindrical tip portion and forming the angular junction between the distal portion of the blunt scraping edge and the substantially planar side of the scraper, such blunt scraping edge extending from said tip portion substantially parallel to the length of the tube a substantial distance toward the proximate end of the tube.

15. An instrument as claimed in claim 9, in which the tube is substantially rigid molded plastic material and the scraper is tapered in direction of projection of the lateral lobe.

16. An instrument as claimed in claim 15, in which the lateral lobe is tapered in a direction generally parallel to the tube bore toward the distal end of the tube.

17. A sampling instrument for collecting cells exfoliated from the uterine cervix of a woman and having a longitudinally elongated aspirator tube with respective proximate and distal ends, the tube having a through bore enabling mucus in the endocervical canal to be sucked into such bore, the distal end portion of the tube forming a scraper and having a distal tip portion insertable into the aperture of the cervix, a lateral lobe projecting transversely of the length of the tube for engagement against the vaginal ring of the cervix, the tube bore opening substantially at the extremity of said distal tip portion, a concave transition section disposed between and joining the inner portion of the lateral lobe and the proximate portion of said distal tip portion, and a blunt scraping edge forming the distal edge of the lateral lobe and the outer edge of said transition section, the lateral lobe having at least one substantially planar lateral side offset from the tube bore and forming with said scraping edge an angular junction, characterized in that the distal tip portion is a flattened frontal lobe including a blunt-nosed, convexly rounded distal tip, the frontal lobe forming part of a flattened portion of the distal end portion of the tube, which flattened portion also forms the lateral lobe, the frontal lobe projecting forward from the lateral lobe a distance sufficient to position said bore opening at approximately the external os when the lateral lobe is in engagement with the vaginal ring of the cervix, the scraping edge also forming a lateral edge of the frontal lobe, and in that the scraping edge is engageable with the inner margin of the vaginal ring of the cervix and positioned to extend across the area of the transformation zone when the lateral lobe is engaged against the vaginal ring of the cervix, so as to enable collection of a scraping sample of exfoliated cells from the transformation zone while the distal tip portion of the tube is inserted for collection of an aspiration sample.

* * * * *